US00PP18105P2

(12) United States Plant Patent
Pieters

(10) Patent No.: US PP18,105 P2
(45) Date of Patent: Oct. 2, 2007

(54) *CHRYSANTHEMUM* PLANT NAMED 'PPP POB LV05'

(50) Latin Name: *Chrysanthemum morifolium*
Varietal Denomination: PPP POB LV05

(75) Inventor: Dirk Pieters, Oostnieuwkerke (BE)

(73) Assignee: Pieters Plant Production, Oostnieuwkerke (BE)

( * ) Notice: Subject to any disclaimer, the term of this patent is extended or adjusted under 35 U.S.C. 154(b) by 0 days.

(21) Appl. No.: 11/414,913

(22) Filed: Apr. 29, 2006

(51) Int. Cl.
*A01H 5/00* (2006.01)

(52) U.S. Cl. ..... Plt./287

(58) Field of Classification Search ..... Plt./287, Plt./293

See application file for complete search history.

*Primary Examiner*—Kent Bell
*Assistant Examiner*—June Hwu

(57) ABSTRACT

A new and distinct *Chrysanthemum* plant cultivar is disclosed, characterized by large decorative type inflorescences, consistent flowering response to short days, blooming consistently after 49 days of short day length, dark lavender ray florets, free branching habit, and a consistent natural season flowering habit during the last week of August, first week of September.

1 Drawing Sheet

Latin name of the genus and species: *Chrysanthemum morifolium.*
Variety denomination: 'PPP POB LV05'.

BACKGROUND OF THE INVENTION

The new cultivar 'PPP POB LV05' is a product of a cross between the female parent 'Molfetta' (which is subject to Plant patent application Status with application No. 09/550,158) and the male parent 'GEDI ONE JAM' (U.S. Plant Pat. No. 13,891). The new cultivar was discovered and selected by Dirk Pieters in September 2003 in Oostnieuwkerke, Belgium.

Asexual reproduction of the new cultivar 'PPP POB LV05' by terminal cuttings and tissue culture was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP POB LV05' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP POB LV05.' These characteristics in combination distinguish 'PPP POB LV05' as a new and distinct *Chrysanthemum* cultivar:

1. Large dark red purple inflorescence;
2. Consistent flowering response to short days, blooming consistently after 49 days of short day length;
3. Free branching habit; and
4. Consistent natural season flowering habit during the last week of August, first week of September.

Plants of the new cultivar 'PPP POB LV05' are similar to plants of the female parent variety, 'Molfetta' in most horticultural characteristics, however plants of the new cultivar 'PPP POB LV05' are taller and wider. Also, the female parent 'Molfetta' has more inflorescences than the new cultivar. Finally, 'Molfetta' has more ray florets per inflorescence and the new cultivar 'PPP POB LV05' has dark red-purple ray florets compared to the red-pink florets of the female parent.

Plants of the new cultivar 'PPP POB LV05' are similar to plants of the male parent 'GEDI ONE JAM' in most horticultural characteristics, however plants of the new cultivar 'PPP POB LV05' are shorter but wider. Also, the male parent has more ray florets per inflorescence. Finally, the new cultivar 'PPP POB LV05' has much darker red-purple ray florets compared to the light pink ray florets of the male parent.

In comparison to the commercially available variety 'GEDI TWO PAD' (U.S. Plant Pat. No. 14,501) 'PPP POB LV05' is taller and has a wider plant spread. Additionally, the new variety 'PPP POB LV05' has more ray florets per inflorescence than the comparable variety. Further, the new variety 'PPP POB LV05' has very dark red-purple ray florets compared to the purple-pink ray florets of 'GEDI TWO PAD.' Finally, the disc florets of 'PPP POB LV05' are bright yellow compared to the yellow-orange of 'GEDI TWO PAD' and 'PPP POB LV05' has less inflorescence per later branch than the comparable variety 'GEDI TWO PAD.'

BRIEF DESCRIPTION OF THE PHOTOGRAPH

The accompanying photograph in FIG. 1 illustrates in full color a typical plant of 'PPP POB LV05' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP POB LV05' plants grown in Oxnard, Ventura County, Calif., during the months of May through September 2005. The growing temperature ranged from 12° C. to 15° C. at night to 12° C. to 20° C. during the day. Measurements and numerical values represent averages of typical flowering types.

Botanical classification: *Chrysanthemum morifolium* cultivar 'PPP POB LV05.'
Commercial classification: Garden-type *Chrysanthemum*.

PROPAGATION

Time to rooting: 7 to 14 days at approximately 21° C.
Root description: Fine, fibrous.

PLANT

Growth habit: Mounding herbaceous perennial.
Height: Approximately 27 cm.
Plant spread: Approximately 48 cm.
Growth rate: Moderate.
Branching characteristics: Free Branching.
Length of lateral branches: Approximately 20 cm.
Number of leaves per lateral branch. Approximately 26.
Age of plant described: Approximately 120 days.

FOLIAGE

Leaf:
- *Arrangement.*—Alternate single.
- *Average length.*—Approximately 5 cm.
- *Average width.*—Approximately 2.9 cm.
- *Shape of blade.*—Ovate.
- *Apex.*—Acuminate.
- *Base.*—Attenuate.
- *Attachment.*—Stalked.
- *Margin.*—Serrate.
- *Texture of top surface.*—Lightly pubescent.
- *Texture of bottom surface.*—Lightly pubescent.
- *Leaf internode length.*—Approximately 2.1 cm.
- *Color.*—Young foliage upper side: Near Green 137A. Young foliage under side: Near Green 137C. Mature foliage upper side: Near Green 137A. Mature foliage under side: Near Green 137C.
- *Venation.*—Type: Palmately net. Venation color upper side: Near Green 137D. Venation color under side: Near Green 137D.

Petiole:
- *Average length.*—Approximately 0.9 cm.
- *Color.*—Near Green 137A.
- *Diameter.*—Approximately 0.3 cm.

BLOOM

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately last week of August, first week of September.
- *Number of inflorescences per lateral branch.*—Approximately 15.
- *Inflorescence diameter.*—Approximately 4.9 cm.
- *Inflorescence depth.*—Approximately 1.9 cm.
- *Inflorescence longevity on plant.*—Approximately 28 to 32 days.
- *Persistence.*—Persistent.

Ray florets:
- *Appearance.*—Matte.
- *Texture.*—Smooth.
- *Average number of ray florets per inflorescence.*—185.
- *Shape.*—Oblanceolate.
- *Aspect.*—Flat.
- *Margin.*—Entire.
- *Apex.*—Obtuse.
- *Length.*—Approximately 1.8 cm.
- *Width.*—Approximately 0.4 cm.
- *Color.*—Upper surface at first opening: Near Red-Purple 59A. Upper surface at maturity: Near Red-Purple 59A. Upper surface at fading: Near Red-Purple 71A. Under surface at first opening: Near Red-Purple 70A. Under surface at maturity: Near Red-Purple 71A. Under surface at fading: Near Purple 76B.

Disc florets:
- *Appearance.*—Shiny.
- *Texture.*—Smooth.
- *Average number of florets per disc.*—Approximately 12.
- *Shape.*—Cylindric.
- *Apex.*—Obtuse.
- *Average length.*—Approximately 0.4 cm.
- *Average width.*—Approximately 0.1 cm.
- *Color.*—At first opening: Near Yellow 9A. At maturity: Near Yellow 9A. At fading: Near Yellow-Orange 15A.

Peduncle:
- *Length.*—At terminal end (shortest): Approximately 7.1 cm. At lateral end (longest): Approximately 9.1 cm.
- *Angle to stem.*—Acute.
- *Strength.*—Moderate.
- *Color.*—Near Green 137C.
- *Habit.*—Upright.
- *Diameter.*—Approximately 0.1 cm.
- *Surface texture.*—Lightly pubescent.

Inflorescence bud:
- *Length.*—Approximately 0.5 cm.
- *Diameter.*—Approximately 0.7 cm.
- *Form.*—Globular.
- *Color.*—Near Green 138C.

Involucral bracts (phyllaries):
- *Appearance.*—Matte.
- *Texture.*—Lightly pubescent:
- *Number.*—Approximately 25.
- *Shape.*—Ovate.
- *Margin.*—Entire.
- *Apex.*—Acute.
- *Length.*—Approximately 0.5 cm.
- *Width.*—Approximately 0.4 cm.
- *Color.*—Upper side: Near Green 137A. Under side: Near Green 137A.

REPRODUCTIVE ORGANS

Ray florets:
- *Number of pistils per floret.*—1.
- *Stigma shape.*—2 branched.
- *Stigma color.*—Near Yellow 9A.
- *Style color.*—Near Yellow-Green 154C.
- *Style length.*—Approximately 0.4 cm.
- *Stamens.*—Absent.

Disc florets:

*Number of pistils per floret.*—1.
*Stigma shape.*—Cylindric.
*Stigma color.*—Near Yellow 9A.
*Style length.*—Approximately 0.1 cm.
*Style color.*—Near Yellow-Green 154D.
*Number of stamens per floret.*—Approximately 5.
*Anther shape.*—Tubular.
*Anther color.*—Near Yellow 9A.
*Pollen color.*—Near Yellow 9A.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP POB LV05' as herein illustrated and described.

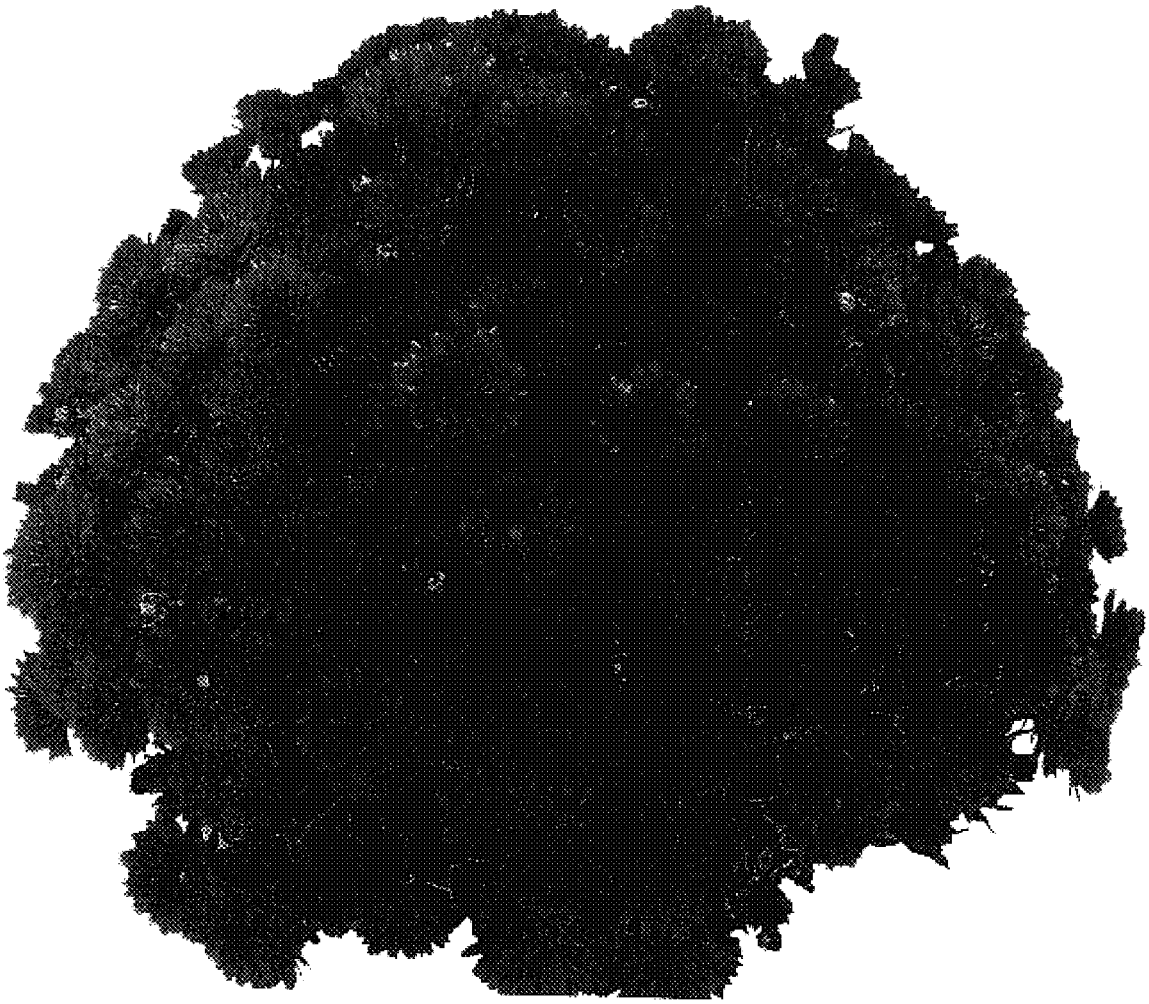

* * * * *